(12) United States Patent
Nifant'ev et al.

(10) Patent No.: US 6,930,190 B2
(45) Date of Patent: Aug. 16, 2005

(54) PROCESS FOR THE PREPARATION OF HETEROCYCLIC PENTALENE DERIVATIVES

(75) Inventors: Ilya E Nifant'ev, Moscow (RU); Vladimir V. Bagrov, Moscow (RU)

(73) Assignee: Basell Polyolefine GmbH, Wesseling (DE)

( * ) Notice: Subject to any disclaimer, the term of this patent is extended or adjusted under 35 U.S.C. 154(b) by 0 days.

(21) Appl. No.: 10/485,497

(22) PCT Filed: Jul. 10, 2002

(86) PCT No.: PCT/EP02/07680

§ 371 (c)(1),
(2), (4) Date: Jan. 30, 2004

(87) PCT Pub. No.: WO03/014107

PCT Pub. Date: Feb. 20, 2003

(65) Prior Publication Data

US 2004/0192931 A1 Sep. 30, 2004

(30) Foreign Application Priority Data

Aug. 1, 2001 (EP) .............................................. 01202930

(51) Int. Cl.⁷ .................... C07D 333/50; C07D 333/74; C07D 307/77; C07D 307/93; C07D 209/04
(52) U.S. Cl. ............................. 549/42; 549/43; 549/49; 549/457; 549/465; 548/516
(58) Field of Search .............................. 549/42, 43, 49, 549/457, 465; 548/516

(56) References Cited

U.S. PATENT DOCUMENTS

| | | | | |
|---|---|---|---|---|
| 4,496,742 A | * | 1/1985 | Smith .......................... | 548/516 |
| 4,532,236 A | * | 7/1985 | Nickolson et al. .......... | 514/184 |
| 4,853,149 A | * | 8/1989 | Krause et al. ......... | 252/299.61 |
| 5,136,081 A | * | 8/1992 | Briner ........................ | 558/412 |
| 5,252,749 A | | 10/1993 | Badorc et al. ................ | 549/51 |
| 5,747,531 A | * | 5/1998 | Matsumura et al. ........ | 514/469 |
| 6,057,316 A | * | 5/2000 | Wrobel et al. ............ | 514/224.5 |
| 6,423,870 B1 | * | 7/2002 | Langlois et al. ............. | 564/219 |
| 6,444,833 B1 | * | 9/2002 | Ewen et al. ................... | 556/11 |
| 6,762,316 B1 | * | 7/2004 | Chand et al. ............... | 560/126 |

FOREIGN PATENT DOCUMENTS

WO    0144318    6/2001    ........... C08F/10/00

OTHER PUBLICATIONS

J. Ewen, "Polymerization Catalysts with Cyclopentadienyl Ligands Ring–Fused Pyrrole and Thiophene Heterocycles," *J. Am. Chem. Soc.*, vol. 120(41), p. 10786–10787 (1998).

N. Chapman et al., "Some Derivatives of 2– and 3–Phenylthiophen;" *J. Chem. Soc.* (J.C.S. Perkin I), vol. 22, p. 2355–2360 (1976).

"7. Reduction of Carbonyl Compounds;" *Comprehensive Organic Transformations*, VCH Publishers, p. 527–552 (ed. 1989).

"34. Dehydration of Alcohols;" *Comprehensive Organic Transformations*, VCH Publishers, p. 151–153 (ed. 1989).

Minoru Ishikura et al., "A Concise Preparation of Yuehchukene and Its Analogues," *Heterocycles*, Elsevier Science Publishers BV, Amsterdam, NL, vol. 53(10), p. 2201–2220 (2000).

Otto Meth–Cohn et al., "Thiophene analogs of indenes. II. Synthesis, tautomerism, and metalation of the thiophene analogs of 2–methylindene," Chemical Abstracts Service, Columbus, OH, *Acta Chem. Scand.*, vol. 20(7), p. 1733–42 (1966).

Maxim et al., *Bulletin de la Societe Chimique Francais*, vol. 5(6), p. 1339–1345 (1939).

\* cited by examiner

*Primary Examiner*—Deborah C. Lambkin
(74) *Attorney, Agent, or Firm*—Cheng Q. Song

(57) ABSTRACT

A process for preparing heterocyclic pentalene derivative having formula (I): wherein w is a sulfur atom (S), an oxygen atom (O) or a NR or PR group, wherein R is an hydrocarbon group; $R^1$, $R^2$, $R^3$, and $R^4$, equal to or different from each other, are hydrogen atoms or hydrocarbon groups; said process comprising the following steps: a) contacting a compound of formula (II) T is a OR, $NR_2$, $CCl_3$, $CF_3$, Cl, Br, I, imidazolil or pirazolyl radical; with at least one molar equivalent of a vinyl compound of formula (III): wherein M is MgHal, Li, K, ZnHal, wherein Hal is chlorine, bromine or iodine; (II), (III) b) treating the compound of formula obtained in step a) with a Bronsted acid; c) treating the compound obtained in step b) with a reducing agent; and d) dehydrating the alcohol obtained in step c) in order to obtain the compound of formula (I).

10 Claims, No Drawings

PROCESS FOR THE PREPARATION OF HETEROCYCLIC PENTALENE DERIVATIVES

This application is the U.S. national phase of International Application PCT/EP02/07680, filed Jul. 10, 2002.

The present invention relates to a new process for preparing heterocyclic pentalenes derivatives of formula:

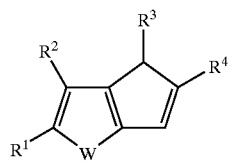

wherein $R^1$, $R^2$, $R^3$ and $R^4$ represent hydrogen or hydrocarbon rests and W is an oxygen atom, a sulfur atom or a NR or PR group and R is an hydrocarbon rest.

Heterocyclic pentalenes are well known in the art for various uses. For example substituted thiophenes and b, d-ortho-fused thiophenes are used as reference materials in the analysis of sulphur-containing substances of fossil raw materials, such as mineral oils, coal, carbonaceous oils, shale oils and tar sands, as model systems for studying the desulphurisation of the aforementioned fossil raw materials, also on a technical scale, as oxidation inhibitors, for example in lubricants and as active substances in the fields involving biocides.

Recently they have been used for the preparation of metallocene complexes useful as catalysts for the polymerization of olefins. For example in J. Am. Chem. Soc. 1998, 120, 10786–10787 Ewen et al. describe metallocene compounds containing thiopentalene and azapentalene derivatives. Also PCT/EP00/12406 describes metallocene compounds containing thiopentalenes ligands. Catalyst based on these compounds produce polypropylene having a high degree of isotacticity. However the synthesis of these compounds involves several steps with low yields and, moreover, some derivatives are not accessible according to the routes proposed in these documents.

Therefore, a new process that permits to obtain these compounds in higher yields and with simple steps would be desirable.

The applicant has now found a new process that permits to overcome the above drawbacks and, moreover, to obtain a broader class of compounds.

An object of the present invention is a process for preparing heterocyclic pentalene derivatives having formula (I):

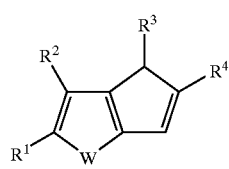

wherein

W is a sulfur atom, an oxygen atom or a NR or PR group wherein R is a linear or branched saturated or unsaturated $C_1$–$C_{20}$-alkyl, $C_3$–$C_{20}$-cycloalkyl, $C_6$–$C_{20}$-aryl, $C_7$–$C_{20}$-alkylaryl or $C_7$–$C_{20}$-arylalkyl radical, optionally containing heteroatoms belonging to groups 13–17 of the Periodic Table of the Elements; preferably the group NR is N-methyl or N-phenyl; and the group PR is P-methyl or P-phenyl; more preferably W is a sulfur atom;

$R^1$, $R^2$, $R^3$ and $R^4$, equal to or different from each other, are hydrogen atoms or a linear or branched saturated or unsaturated $C_1$–$C_{20}$-alkyl, $C_3$–$C_{20}$-cycloalkyl, $C_6$–$C_{20}$-aryl, $C_7$–$C_{20}$-alkylaryl or $C_7$–$C_{20}$-arylalkyl radical, optionally containing heteroatoms belonging to groups 13–17 of the Periodic Table of the Elements; or $R^1$ and $R^2$ and/or $R^3$ and $R^4$ can form a $C_4$–$C_7$ ring optionally containing O, S, N, P or Si atoms, said ring optionally bearing $C_1$–$C_{20}$ alkyl substituents or being optionally fused with a $C_4$–$C_7$ ring optionally containing O, S, N, P or Si atoms, such as a benzene or a cyclopentadiene ring; preferably $R^1$ is hydrogen, a $C_1$–$C_{20}$-alkyl or $C_7$–$C_{20}$-arylalkyl radical; more preferably $R^1$ is a methyl, a phenyl or a $C_1$–$C_{10}$ alkyl substituted phenyl radical; preferably $R^2$ is hydrogen or a $C_7$–$C_{20}$-arylalkyl radical; more preferably $R^2$ is a phenyl or a $C_1$–$C_{10}$ alkyl-substituted phenyl radical; preferably $R^3$ is hydrogen or a $C_1$–$C_{20}$-alkyl radical; and preferably $R^4$ is hydrogen, a $C_1$–$C_{20}$-alkyl or $C_7$–$C_{20}$-arylalkyl radical; more preferably $R^4$ is a methyl, or a phenyl radical;

said process comprising the following steps:

a) contacting a compound of formula (II):

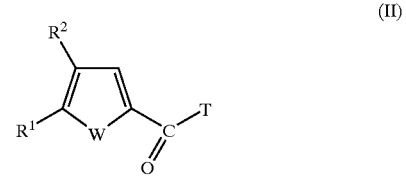

wherein $R^1$ and $R^2$ are defined as above and T is a OR, $NR_2$, OH, $CCl_3$, $CF_3$, Cl, Br, I, imidazolyl or pirazolyl radical;

with at least one molar equivalent of a vinyl compound of formula (III):

wherein $R^3$ and $R^4$ are defined as above and M is MgHal, Li, K, ZnHal, wherein Hal is chlorine, bromine or iodine; to form a compound of formula (IV):

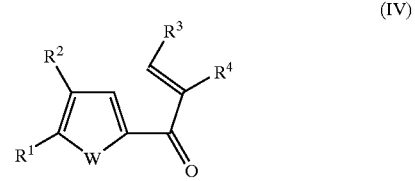

b) treating the compound of formula (IV) with a Brønsted acid to form a compound of formula (V):

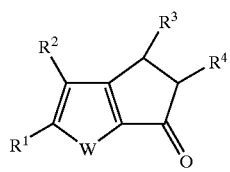
(V)
c) treating the compound of formula (V) with a reducing agent to form the correspondent alcohol of formula (VI);
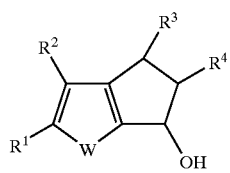
(VI)
and
d) dehydrating the alcohol of formula (VI).
Non limitative examples of compounds of formula (I) are:
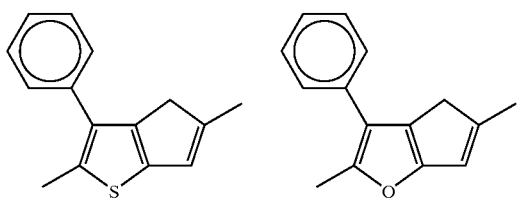
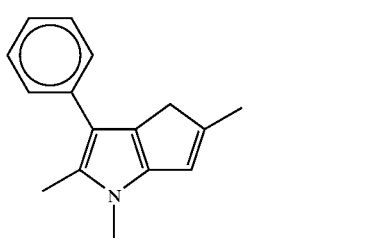
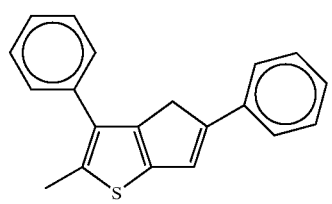
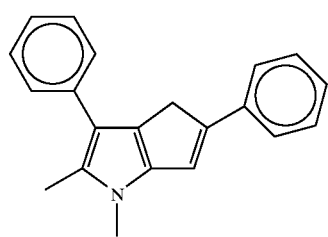
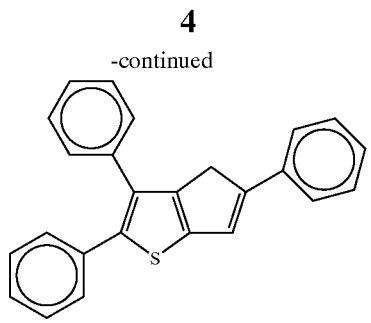
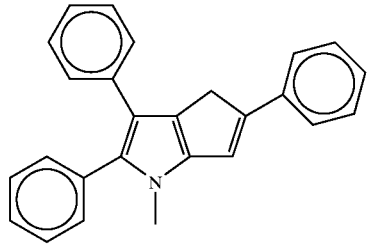
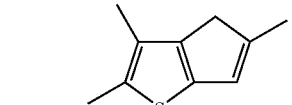
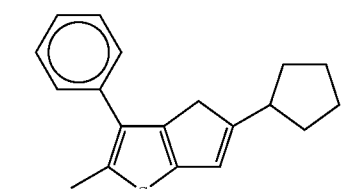
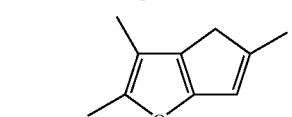
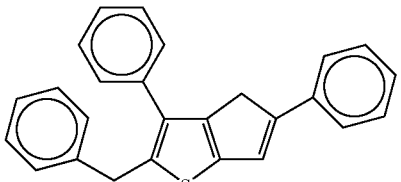
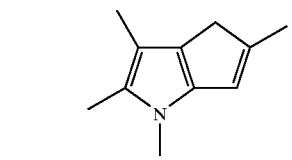
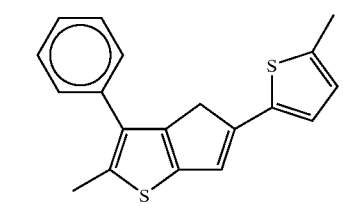
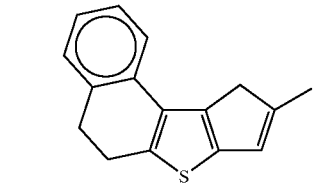

-continued

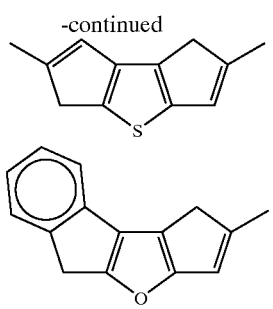

Compounds of formula (II) used in step a) can be prepared with methods generally known in the art. For example when W is a sulfur atom these compounds can be prepared according to the process described in J. Chem Soc. Perkin 1, 1976, vol. 22, 2355–2360.

Compounds of formula (III) can be easily prepared starting from the correspondent vinyl bromide or they can be purchased as such.

Step a) is carried out at a temperature range of from −78 C to 100° C., preferably from −20° C. to 20° C. Usually aprotic solvents are used, such as toluene, diethyl ether, hexane, tetrahydrofuran, dimethyl formamide, etc. The product obtained from step a) is purified by process known in the art such as filtration, crystallization, chromatography, distillation; otherwise it is used as such.

Preferably in the compound of formula (II) T is a $NR_2$ group; more preferably T is a $N(Me)_2$ or a $N(Et)_2$ radical. In the compound of formula (III) preferably the group M is MgBr or Li. Examples of Brønsted acid used in step b) are methanesulphonic acid, sulfuric acid, phosphoric acid, polyphosphoric acid or $P_2O_5$/methansulfuric acid. Preferably methanesulphonic acid or sulfuric acid are used. The reaction is preferably carried out in water or in an organic solvent such as dichloromethane, diethyl ether, tetrahydrofuran, dimethyl formamide, or in mixtures of water and organic solvents optionally in the present of a phase transfer agent. The reaction is carried out at a temperature range from 0° C. to 100° C. The amount of acid in step b) depends from the acid, usually a large excess of acid is used for example from 10 to 10000 equivalents or more.

The product obtained from step b) is purified by processes known in the art such as filtration, crystallization, chromatography, distillation; otherwise it is used as such.

Examples of reducing agents that can be used in step c) can be found in "Comprehensive Organic Transformations" ed. 1989 VCH Publishers pages 527–552. For example $LiAlH_4$, $AlH_3$, $NaBH_4$ or $LiHAl(OtBu)_3$ can be used. Preferably $LiAlH_4$ is used.

The type of solvent used in step c) depends from the reducing agent used. In the case of $LiAlH_4$, $AlH_3$, $NaBH_4$ or $LiHAl(OtBu)_3$ the reaction is carried out in an aprotic solvent such as toluene, diethyl ether, hexane, tetrahydrofuran, dimethyl formamide, at a temperature range of from −78 C to 100° C., preferably from 0° C. to 80° C. The product obtained from step c) is purified by processes known in the art such as filtration, crystallization, chromatography, distillation; otherwise it is used as such.

Step d) is carried out by treating the alcohol of formula (VI) with a dehydrating agent. Examples of dehydrating agent can be found in "Comprehensive Organic Transformations" ed. 1989 VCH Publishers pages 151–153. Example of dehydrating agent are p-toluenesulfonic acid, sulfuric acid, hydrochloric acid and iodine. Preferably p-toulensulfonic acid and iodine are used.

The amount of dehydrating agent depends from the dehydrating agent used. It can vary from one equivalent to a large excess such as 1000 equivalents and more.

The type of solvent used in step d) depends from the dehydrating agent used. In the case of p-toulensulfonic acid the reaction is carried out in an aprotic solvent such as toluene, diethyl ether, hexane, tetrahydrofuran, dimethyl formamide, at a temperature range of from 0° C. to 100° C., preferably from 20° C. to 80° C. The product obtained from step d) is purified by processes known in the art such as filtration, crystallization, chromatography, distillation. A further method for purifying compounds obtained in step d) is treating the crude reaction product with at least one equivalent of an organolithium compound such as butyllithium, methyllithium, tertbuthylithium and phenyllithium and filtering the obtained salt.

Steps a), b), c) and d) of the process of the present invention may be carried out in sequence without purification of the intermediate products.

Preferably steps c) and d) are carried out "one pot", i.e. without purification of the alcohol of formula (VI).

Compounds of formula (I) can be used as ligands for the synthesis of metallocene complexes, such as those described in WO 01/44318. These complexes are useful as catalyst components for polymerizing alpha-olefins. The syntheses of the metallocene compounds starting from the compounds of the present invention are described in the above mentioned application. Generally, the compounds of formula (I) can be treated with a base and then contacted with a compound of formula YL'Cp wherein Y is halogen, preferably chlorine, L' is a suitable bridge and Cp is a substituted or unsubstituted cyclopentadienyl radical. The obtained bridged ligand is then treated with two equivalents of a base and contacted with the compound of formula $ML''_4$ wherein M is titanium, zirconium or hafnium and L is generally halogen, preferably chlorine. For unbridged metallocene compounds the compound of formula (I) is treated with a base and then the correspondent anion is contacted with a compound of formula $ML''_4$.

The following examples are given for illustrative purposes and are not intended to limit the scope and spirit of the invention.

EXAMPLES

General Procedures.

Operations moisture sensitive were performed under nitrogen by using conventional Schlenk-line techniques. Solvents were purified by degassing with $N_2$ and passing over activated (8 hours, $N_2$ purge, 300° C.) $Al_2O_3$, and stored under nitrogen. n-BuLi (Aldrich) was used as received.

Example 1

Synthesis of 2,3-diphenyl-5-methyl-6H-cyclopenta[b]thiophene

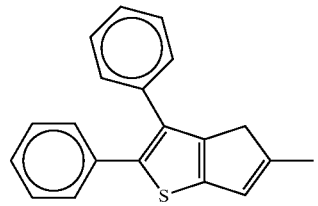

Preparation of the Compound of Formula (II)

Synthesis of 2,3-Diphenyl-thienylcarbonyc acid

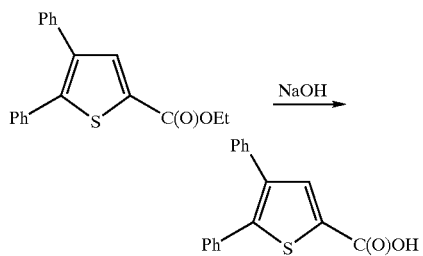

30.8 g (0.1 mol) of 2,3-diphenyl-5-carbetoxythiophene (prepared analogously to 2-methyl-3-phenyl-5-carbetoxythiophene with 70–80% yield from dezoxybenzoin) was treated with solution of 20 g NaOH in 50 ml water+50 ml ethanol. Resulting mixture was refluxed in 3 h and then was treated with 100 ml water. Aqueous phase was collected, added with HCl aq. up to pH=3. White solid was isolated by filtration, washed with 100 ml water and dried. Yield 100%.

$^1$H NMR (Dimethylsulfoxide (DMSO)-$d_6$): 7.76 (s, 1H), 7.40–7.20 (m, 10H), 3.5 (br.s., water+acidic proton)

Synthesis of 2,3-Diphenyl-thienylcarbonyc acid dimethylamide

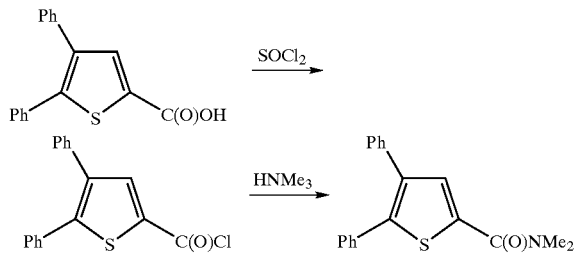

10 g (36 mmol) of acid, 5.5 ml SOCl$_2$ (75 mmol), 0.1 ml dimethylformamide (DMF) and 50 ml of benzene were placed into the bulb and refluxed in 2 h. Then the mixture was evaporated. Resulting oil was dissolved in 10 ml of tetrahydrofuran (THF) and this solution was added dropwise to 30 ml 33% aqueous Me$_2$NH at 0° C. The mixture was stirred in 30 min. The precipitate was isolated, washed with water and dried. Yield 10 g (92%).

$^1$H NMR (CDCl$_3$): 7.45 (s, 1H), 7.40–7.20 (m, 10H), 3.40–3.20 (br.s., 6H)

Step a) 1-(4,5-Diphenyl-2-thienyl)-2-methyl-2-propen-1-on

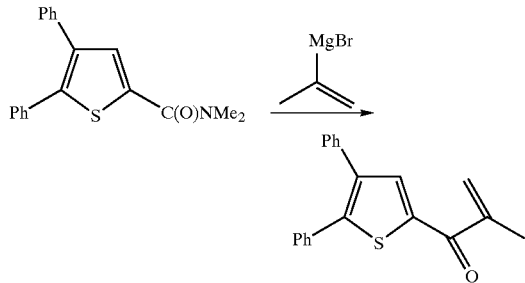

10 g (33 mmol) of 2,3-Diphenyl-thienylcarbonic acid dimethylamide was dissolved in 15 ml THF and the resulting solution was added dropwise to solution of propenylmagnesium bromide prepared from 0.78 g Mg (33 mmol) and 4 g 2-bromopropene (33 mmol) in 50 ml THF at −40° C. The mixture warmed to r.t. and was stirred in 4 h. The resulting solution was poured into 100 ml of 5% aqueous HCl. The organic layer was collected, washed with water, dried over MgSO$_4$ and evaporated to give yellow-reddish oil. Yield 9.5 g (100%). The product is contaminated with 5–10% of starting amide (by NMR) and can be used without further purification.

Step b) 5-Methyl-2,3-diphenyl-4,5-dihydro-6H-cyclopenta[b]thiophen-6-on

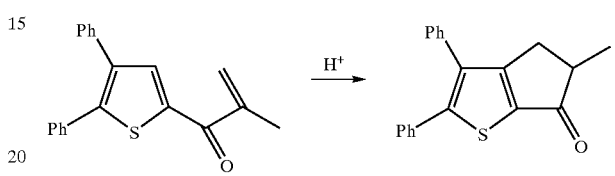

Solution from previous experiment was poured into 80 ml methanesulphonic acid (can be replaced by H$_2$SO$_4$) at 65° C. After 30 min of stirring at reflux the resulting mixture was poured into 400 ml water/300 ml dichlorometane mixture. The organic phase was collected, washed with aq. NaHCO$_3$ up to neutral reaction and dried over MgSO$_4$. The resulting solution was evaporated to give 8.8 g viscous oil. This substance either have to be purified by chromatography on silica gel with benzene as an eluent (R$_f$ of the product is ~0.15) or can be used as is.

$^1$H NMR (CDCl$_3$): 7.40–7.20 (m, 10H), 3.20 (dd, 1H), 3.06 (quintet of doublets, 1H), 2.67 (dd, 1H), 1.44 (d, 3H)

Steps c) and d) 5-Methyl-2,3-diphenyl-4H-cyclopenta[b]thiophene

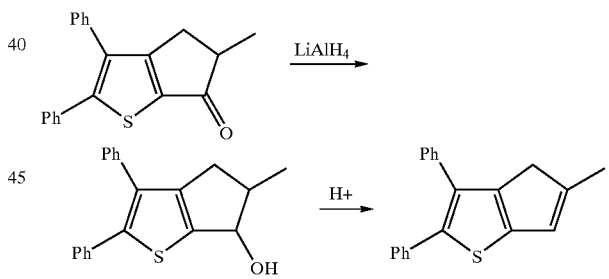

Solution of 7 g (0.023 mol) 5-methyl-2,3-diphenyl-4,5-dihydro-6H-cyclopenta[b]thiophen-6-on in 200 ml ether was treated with 0.24 g (0.0063 mol) LiAlH$_4$ in 100 ml ether. The mixture was stirred in 30 min and then was poured in 300 ml of 10% NH$_4$Cl. The organic phase was collected, dried over MgSO$_4$ and evaporated. Resulting alcohol (6.7 g, 95%) was dissolved in 350 ml benzene. To this solution 0.25 g p-toluenesulphonic acid and a few crystals of 2,6-di(tert-butyl)phenol were added. The resulting mixture was refluxed in 10 min, then was cooled to r.t., washed with saturated aq. NaHCO$_3$ and water. The solution so-obtained was dried over MgSO$_4$ and evaporated. The residue was recrystallized from hexane to give 4.2 g (67% from ketone) of the product as yellowish crystalline solid.

$^1$H NMR (C$_6$D$_6$): 7.45 (d, 2H), 7.31 (d, 2H), 7.15–6.90 (m, 6H), 6.20 (quintet, 1H); 2.73 (br.s, 2H); 1.80 (s, 3H)

Example 2

Synthesis of 2-methyl-3,5-diphenyl-6H-cyclopenta[b]thiophene

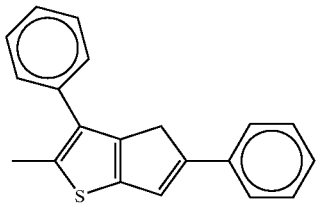

Preparation of the Compound of Formula (II)

Synthesis of 3-chloro-2-phenyl-2-butenal

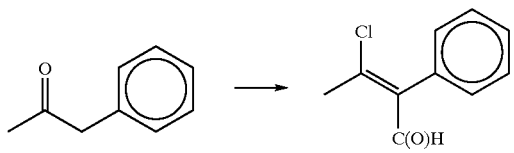

0.375 mol (35 mL) of POCl$_3$ was added at 0° C. to a 0.45 mol (35 mL) of DMF. At the end of the addition, the mixture was allowed to warm up to room temperature and stirred for 30 min. Then it was cooled again to 0° C. and carefullly treated with 0.15 mol (20.1 g) of phenylacetone. The resulting reaction mixture was stirred at the same temperature for 1 h and then at 60–70° C. in additional 4 hours (the reaction was monitored by NMR). The resulting viscous solution was poured into a mixture of ice and aqueous sodium acetate (150 g). Product was extracted with CH$_2$Cl$_2$ (3×50 mL). The organic phase was separated, washed with water until neutral pH, dried over MgSO$_4$ and evaporated to dryness. The residue represents chloroaldehyde as a mixture of two forms (ratio of forms depends on the duration of chlorocarbonylation). It was used without further purification. Yield 19.2 (71%).

$^1$H-NMR (CDCl$_3$): 10.47(s) and 10.15(s) (1H, CHO); 7.40–7.00 (group of multiplets, 5H, aromatic CH); 2.79(s) and 2.32(s) (3H, CH$_3$).

Note: do not use distillation to purify the product!

Synthesis of 5-methyl-4-phenyl-2-thiophene-ethylcarboxylate

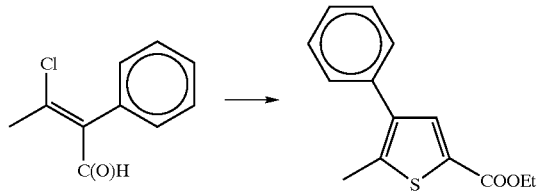

Ethyl-2-mercaptoacetate (45.8 mmol, 5.0 mL) was added at 0° C. to a solution of sodium ethoxide (46 mmol, 3.13 g) in 50 mL of ethanol and the resulting mixture was stirred at the same temperature for 30 min. Then 3-chloro-2-phenyl-2-butenal (45.8 mmol, 8.3 g) was added and stirring was continued overnight. The resulting product was refluxed for 2 h, cooled to room temperature and diluted in 100 mL of water. The organic layer was collected and the water layer was extracted with CH$_2$Cl$_2$ (3×50 mL). The combined organic layers were dried over MgSO$_4$, evaporated to dryness and the residue was used in the next step without further purification.

Synthesis of 5-methyl-4-phenyl-2-thiophenecarboxylic acid

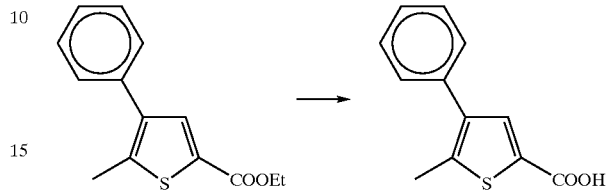

The 5-methyl-4-phenyl-2-thiophene-ethylcarboxylate coming from the previous step was added to a 30% solution of sodium hydroxide in 100 mL of ethanol and the resulting mixture was refluxed for 2 h. Then it was diluted in water and extracted with 50 mL of benzene. The water phase was isolated, acidified and the mixture was filtered. The precipitate was dried under P$_2$O$_5$. Yield 9.5 g (95% towards 3-chloro-2-phenyl-2-butenal).

$^1$H-NMR (CDCl$_3$): 12.00–10.00 (br.s, 1H, COOH); 7.87 (s, 1H, thiopheneCH); 7.50–7.35 (m, 5H, phenylCH); 2.58 (s, 3H, CH$_3$).

Synthesis of 2-Methyl-3-phenyl-thienylcarbonyc dimethylamide

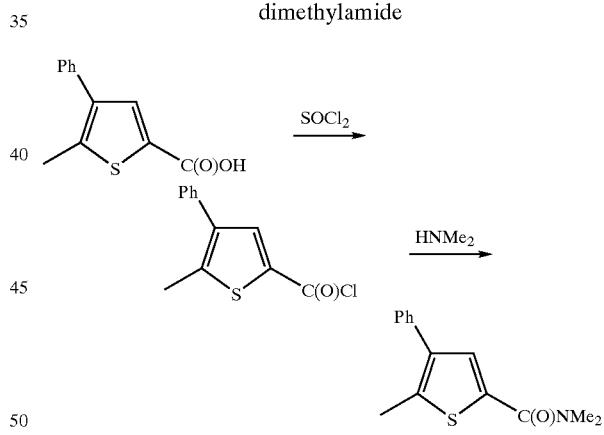

21.8 g (0.1 mol) of acid, 10.9 ml SOCl$_2$ (0.5 mmol), 0.5 ml DMF and 150 ml of dichloromethane were placed into the bulb and refluxed in 2 h. Then the mixture was evaporated. Resulting oil was dissolved in 20 ml THF and this solution was added dropwise to 50 ml 33% aqueous Me$_2$NH at 0° C. The mixture was stirred in 30 min. The resulting emulsion was poured into 500 ml of water. Product was extracted with 2×50 ml dichloromethane. Solution was washed with water, dried over magnesium sulfate and evaporated to give brown viscous liquid that tends to crystallize. Yield 28 g (81%).

$^1$H NMR (CDCl$_3$): 7.45 (s, 1H), 7.40–7.20 (m, 10H), 3.40–3.20 (br.s., 6H)

Step a) 1-(5-Methyl-4-phenyl-2-thienyl)-2-phenyl-2-propen-1-on

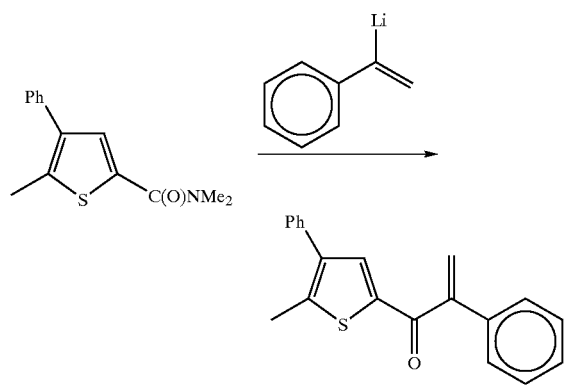

23.3 g (100 mmol) of 2-methyl-3-phenyl-thienylcarbonic acid dimethylamide was mixed with 100 ml ether and the resulting suspension was added in some portions at 0° C. to solution of 1-stiryllitium prepared from 62 ml 1.6M BuLi in hexane (100 mmol) and 27 g 1-bromostyrene (150 mmol) in 200 ml ether. The mixture warmed to r.t. and was stirred in 1 h. The resulting solution was poured into 500 ml of 5% aqueous HCl. The organic phase was collected, separated from insoluble impurities (these impurities presumably are due to the use of Li-derivative instead of Mg derivative in the previous case), washed with water, dried over MgSO$_4$ and evaporated to give yellow oil. Yield of crude product 15 g (52%). The product can contaminated with 5–10% of starting amide (by NMR) and can be used without further purification.

$^1$H NMR (CDCl$_3$): 7.61 (s, 1H), 7.55–7.35 (m, 10H), 6.03 (s, 1H), 5.82(s, 1H), 2.59 (s., 3H)

Step b) 2-Methyl-3,5-diphenyl-4,5-dihydro-6H-cyclopenta[b]thiophen-6-on

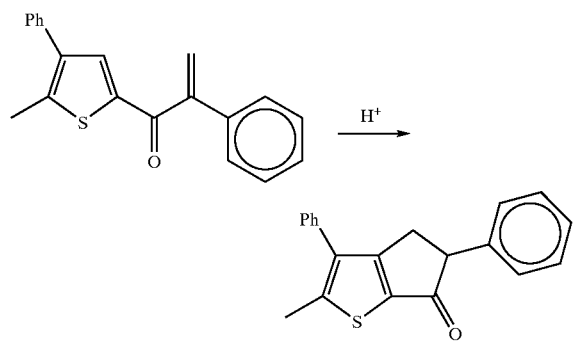

Vinyl-ketone obtained in previous experiment was dissolved in 20 ml of dichloromethane and resulting was poured into 50 ml methanesulphonic acid heated to 65° C. After 30 min of stirring at reflux the resulting mixture was poured into the mixture 0.3l water/ice/200 ml dichlorometane. The organic phase was collected, washed with water, then with aq. NaHCO$_3$ up to neutral reaction and dried over MgSO$_4$. The resulting solution was evaporated to give 14 g of viscous oil. This oil crystallizes on standing. This substance can be used for further steps (reduction by LiAlH$_4$ followed by dehydration without special purification.

$^1$H NMR (CDCl$_3$): 7.55–7.20 (m, 10H), 4.15 (dd, 1H); 3.50 (dd, 1H); 3.07 (dd, 1H), 261 (s., 3H)

Steps c) and d) 2-Methyl-3,5-diphenyl-4H-cyclopenta[b]thiophene

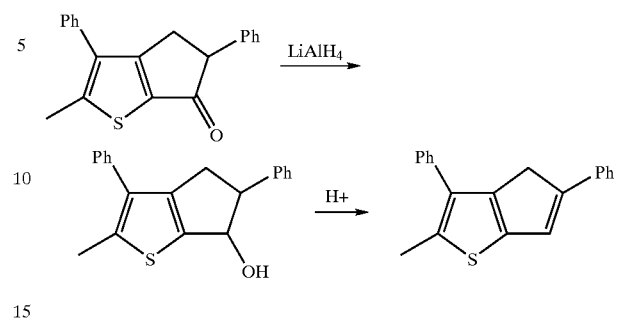

Solution of 14 g (47 mmol) 2-Methyl-3,5-diphenyl-4,5-dihydro-6H-cyclopenta[b]thiophen-6-on in 150 ml ether was treated with 0.63 g (16 mmol) LiAlH$_4$ in 100 ml ether. The mixture was stirred in 30 min and then was poured in 300 ml of 10% NH$_4$Cl. The organic phase was collected, dried over MgSO$_4$ and evaporated. Resulting alcohol (13.4 g, 95%) was poured into solution 1 g p-toluenesulphonic acid in 1l toluene at 65° C. The resulting mixture was stirred in 20 min at 80° C., then it was cooled to r.t., washed with saturated aq. NaHCO$_3$ and water. The solution so-obtained was dried over MgSO$_4$ and evaporated. The residue was isolated by chromatography on silica-gel (hexane/CH$_2$Cl$_2$ 3/1) to give 6.5 g (53% from ketone) of yellowish crystalline solid. This solid consists of two isomers of position of double bond.

$^1$H NMR (CDCl$_3$): 7.60–7.20 (m, 10H), 7.21(m) and 7.14(m) (1H), 3.83 (br.s) and 3.68 (br.s) 2H); 2.60 (s, 3H)

Example 3

Synthesis of 2,3,5-triphenyl-6H-cyclopenta[b]thiophene

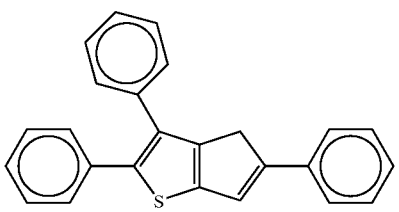

Preparation of the Compound of Formula (II)

2,3-diphenyl-thienylcarbonic acid dimethylamide was prepared in analogous manner to 2-Methyl-3-phenyl-thienylcarbonyc dimethylamide with the exception that the starting compound was dibenzyl ketone instead of phenylacetone.

Step a) 1-(4,5-Diphenyl-2-thienyl)-2-phenyl-2-propen-1-on

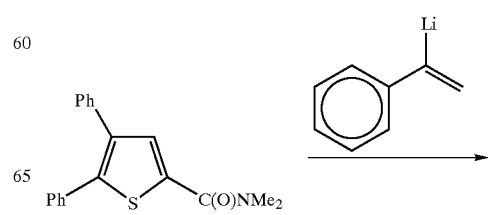

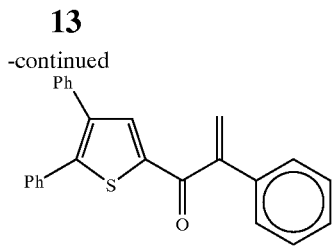

30.7 g (100 mmol) of 2,3-diphenyl-thienylcarbonic acid dimethylamide was mixed with 100 ml ether and the resulting suspension was added in some portions at 0° C. to solution of 1-stiryllitium prepared from 62 ml 1.6M BuLi in hexane (100 mmol) and 27 g 1-bromostyrene (150 mmol) in 200 ml ether. The mixture warmed to room temperature (r.t.) and was stirred for 1 h. The resulting solution was poured into 500 ml of 5% aqueous HCl. The organic phase was collected, separated from insoluble impurities, washed with water, dried over MgSO$_4$ and evaporated to give 20.9 g (57%) of crystalline solid. The product can be contaminated with 5–10% of starting amide (by NMR) and can be used without further purification.

$^1$H NMR (CDCl$_3$): 7.82 (s, 1H), 7.70–7.30 (m, 15H), 6.16 (s, 1H), 5.96(s, 1H)

Note: only technical-grade 1-bromo-styrene is available. It was distilled before reaction and was taken in 50% excess.

Step b) 2,3,5-triphenyl-4,5-dihydro-6H-cyclopenta[b]thiophen-6-on

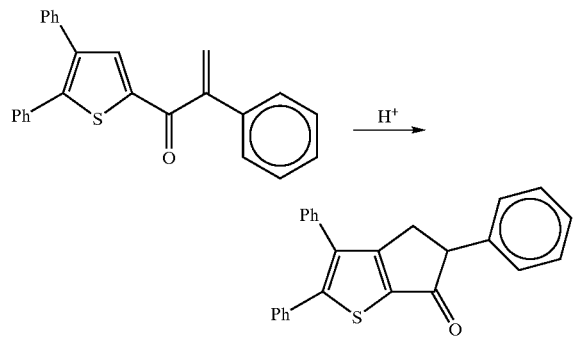

Vinyl-ketone obtained in previous experiment was dissolved in 20 ml of dichloromethane and resulting was poured into 50 ml methanesulphonic acid heated to 65° C. After 30 min of stirring at reflux the resulting mixture was poured into the mixture 0.31 water/ice/200 ml dichloromethane. The organic phase was collected, washed with water, then with aq. NaHCO$_3$ up to neutral reaction and dried over MgSO$_4$. The resulting solution was evaporated to give 20 g of crystalline product. This substance can be used for further steps (reduction by LiAlH$_4$ followed by dehydration) without special purification.

$^1$H NMR (CDCl$_3$): 7.55–7.20 (m, 15H), 4.25 (dd, 1H); 3.61 (dd, 1H); 3.20 (dd, 1H)

Steps c) and d) 2,3,5-Triphenyl-4H-cyclopenta[b]thiophene

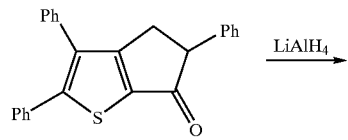

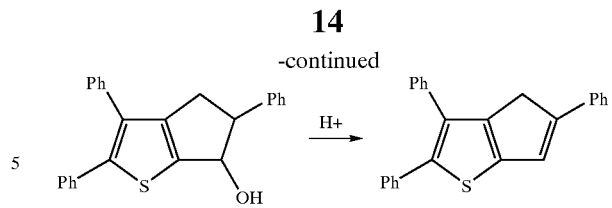

Solution of 3.7 g (10 mmol) 2,3,5-triphenyl-4,5-dihydro-6H-cyclopenta[b]thiophen-6-on in 20 ml ether was treated with 130 mg (16 mmol) LiAlH$_4$ in 10 ml ether. The mixture was stirred in 30 min and then was poured in 50 ml of 10% NH$_4$Cl. The organic phase was collected, dried over MgSO$_4$ and evaporated. Resulting alcohol was poured into solution of 300 mg p-toluenesulphonic acid in 300 ml toluene at 65° C. The resulting mixture was refluxed in 20 min, then it was cooled to r.t., washed with saturated aq. NaHCO$_3$ and water. The solution so-obtained was dried over MgSO$_4$ and evaporated. The residue was isolated by chromatography on silica-gel (hexane/CH$_2$Cl$_2$ 3/1) to give 2.1 g (60% from ketone) of yellowish crystalline solid.

$^1$H NMR (CDCl$_3$): 7.60 (m, 2H), 7.45–7.25(m, 14H); 3.72 (d, 2H)

Example 3

Synthesis of 2,5-dimethyl-3-(4-chloro-phenyl)-6H-cyclopenta[b]thiophene

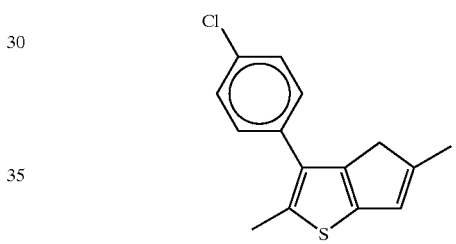

Preparation of the Compound of Formula (II)

Synthesis of (4-chloro-phenyl)-acetone

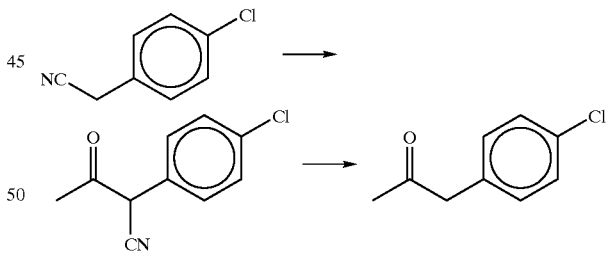

34 g (0.224 mol) (4-chloro-phenyl)benznitryl and 33 ml (0.337 mol) ethylacetate was added to the hot solution of 24 g (0.3 mol) sodium isopropilate in 150 ml isopropanol. Reaction mixture was stirred at reflux in 3 hours then it was cooled to r.t., treated with 20 g (0.3 mol) acetic acid and finally diluted with 500 ml water. Organic precipitate was extracted with 100 ml dichloromethane. Resulting solution was evaporated to give yellowish solid of p-Cl-phenylacetone that was used without purification.

$^1$H-NMR (CDCl$_3$): 7.44 (AA'BB' component, 2H); 7.36 (AA'BB' component, 2H); 4.68 (s, 1H); 2.31 (s, 3H).

p-Cl-phenylacetone prepared in previous experiment was added in small portions to 50 ml of concentrated sulfuric acid at 0–5° C. then the mixture was heated at stirring to 100° C. in 10 min. Then the reaction mixture was cooled to 0° C., was treated quickly with 250 ml water and was stirred at 100° C. in 3 hours. The resulting mixture was cooled to r.t., the organic layer was separated and distilled at 108–110/10 torr to give 24.5 g (65% from p-Cl-phenylacetone).

$^1$H-NMR (CDCl$_3$): 7.34 (AA'BB' component, 2H); 7.16 (AA'BB' component, 2H); 3.71 (s, 2H); 2.20 (s, 3H).

Synthesis of 5-methyl-4-(4-Cl-phenyl)1-2-thiophenecarboxylic acid

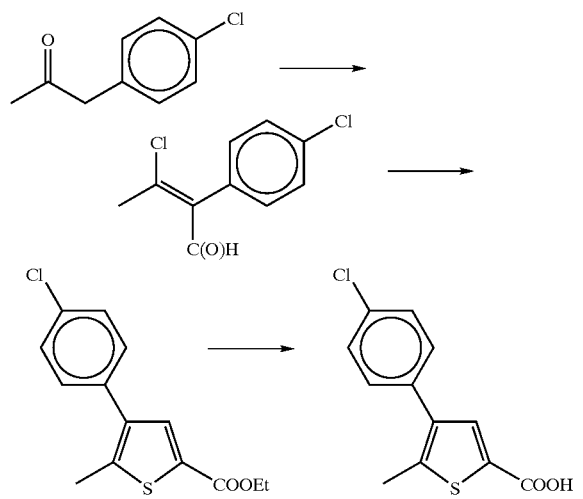

17.5 ml (0.19 mol) of POCl$_3$ was added at 0° C. to a 32 ml (0.44 mol) of DMF. At the end of the addition, the mixture was allowed to warm up to room temperature and stirred for 30 min. Then it was cooled again to 0° C. and carefully treated with 24.5 g (0.145 mol) of p-Cl-phenylacetone. The resulting reaction mixture was stirred at the same temperature for 1 h and then at 60–70° C. in additional 4 hours. The resulting viscous solution was poured into a mixture of ice and aqueous sodium acetate (150 g). Product was extracted with CH$_2$Cl$_2$ (3×50 mL). The organic phase was separated, washed with water until neutral pH, dried over MgSO$_4$ and evaporated to dryness. The residue represents 21.5 g (68%) of crude chloroaldehyde that was used as is.

Ethyl-2-mercaptoacetate (12 g, 0.1 mol) was added at 0° C. to a solution of sodium ethoxide (6.8 g, 0.1 mol) in 150 mL of ethanol and the resulting mixture was stirred at the same temperature for 30 min. Then chloroaldehyde from the previous experiment (21.5 g, 0.1 mol) was added and stirring was continued overnight. The resulting product was refluxed for 2 h, cooled to room temperature and then was treated with solution of 12 g (0.3 mol) NaOH in 20 ml water. The resulting mixture was refluxed in 1 hour, then it was cooled to r.t. and finally was poured into 500 ml of water. The resulting mixture was neutralized by aqueous HCl, the precipitate was isolated, washed twice with 200 ml water and dried. Yield 15.3 g (60%).

$^1$H-NMR (DMSO): 7.52 (s, 1H, thiopheneCH); 7.47 (m, 4H, phenylCH); 2.46 (s, 3H, CH$_3$).

Synthesis of 2-Methyl-3-(4-chloro-phenyl)-thienylcarbonyc dimethylamide

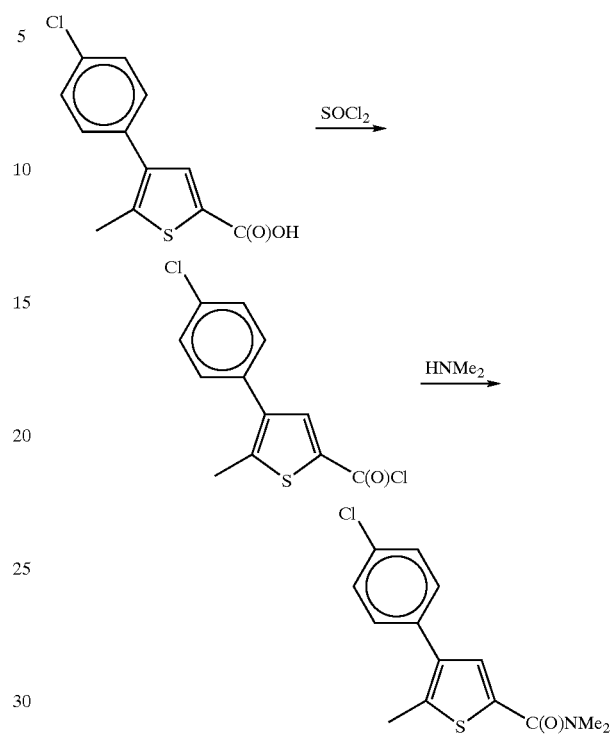

15.3 g (0.06 mol) of acid, 7.1 ml SOCl$_2$ (0.1 mmol), 0.1 ml DMF and 100 ml of dichloromethane were placed into the bulb and refluxed in 30 min. Then the mixture was evaporated. Resulting oil was dissolved in 20 ml THF and this solution was added dropwise to 50 ml 33% aqueous Me$_2$NH at 0° C. The mixture was stirred in 30 min. The resulting emulsion was poured into 500 ml of water. Product was extracted with 2×50 ml dichloromethane. Solution was washed with water, dried over magnesium sulfate and evaporated to give brown viscous liquid. Yield 14.4 g (86%).

$^1$H-NMR (CDCl$_3$): 7.45–7.30 (m, 5H); 3.25 (br.s, 6H); 2.50 (s, 3H).

Step a) 1-[5-Methyl-4-(4-chloro-phenyl)-2-thienyl]-2-methyl-2-propen-1-on

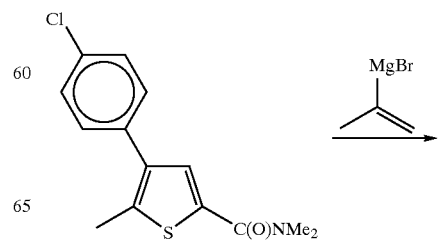

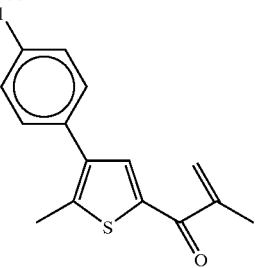

7.2 g (26 mmol) of 2-methyl-3-(p-Cl-phenyl)-thienylcarbonic acid dimethylamide was dissolved in 15 ml THF and the resulting solution was added dropwise to solution of 2-propenylmagnesium bromide prepared from 1 g Mg (42 mmol) and 3.7 g 2-bromopropene (31 mmol) in 20 ml THF at 0° C. The mixture warmed to r.t. and was stirred in 4 h. The resulting solution was poured into 100 ml of 5% aqueous HCl. The organic layer was collected, washed with water, dried over MgSO$_4$ and evaporated to give quantitative amount yellow-reddish oil that was used without further purification.

$^1$H NMR (CDCl$_3$): 7.56 (s, 1H); 7.39 (AA'BB' component, 2H); 7.29 (AA'BB' component, 2H); 5.79 (m, 1H), 5.74(m, 1H), 2.51 (s., 3H); 2.04 (m, 3H)

Step b) 2,5-Dimethyl-3-(4-chloro-phenyl)-4,5-dihydro-6H-cyclopenta[b]thiophen-6-on

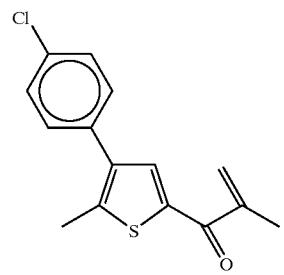

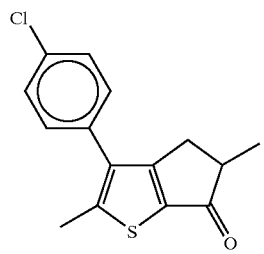

Vinyl-ketone obtained in previous experiment was dissolved in 10 ml of dichloromethane and resulting solution was poured into 25 ml methanesulphonic acid heated to 65° C. After 20 min of stirring at reflux the resulting mixture was poured into the mixture 0.2 l water/ice/50 ml dichloromethane. The organic phase was collected, washed with water, then with aq. NaHCO$_3$ up to neutral reaction and dried over MgSO$_4$. The resulting solution was evaporated and was purified by chromatography (hexane/ether 3/1) to give 2.2 g (31%) of viscous oil.

$^1$H NMR (CDCl$_3$): 7.41 (AA'BB' component, 2H); 7.23 (AA'BB' component, 2H); 3.13 (dd, 1H), 2.94 (quintet of doublets, 1H); 2.50 (s, 3H); 2.49 (dd, 1H), 1.31 (d, 3H)

Steps c) and d) Synthesis of 2,5-dimethyl-3-(4-chlorophenyl)-6H-cyclopenta[b]thiophene

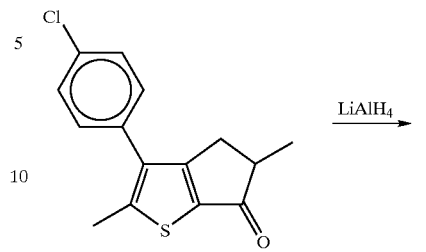

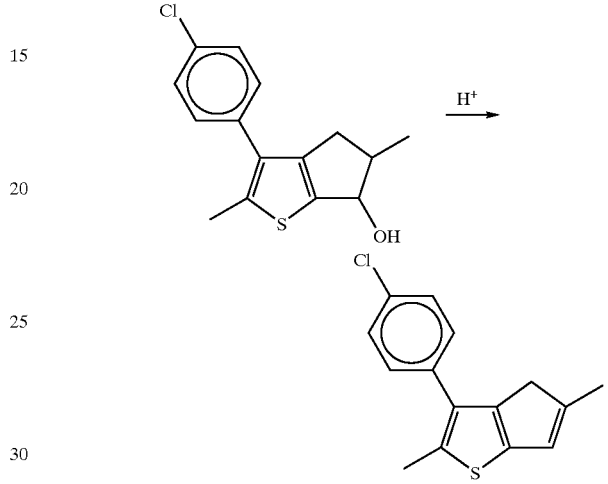

Solution of 2.2 g (8 mmol) 2,5-dimethyl-3-(4-chlorophenyl)-4,5-dihydro-6H-cyclopenta[b]thiophen-6-on in 20 ml ether was treated with 0.1 g (2.6 mmol) LiAlH$_4$ in 20 ml ether. The mixture was stirred in 30 min and then was poured in 30 ml of 10% NH$_4$Cl. The organic phase was collected, dried over MgSO$_4$ and evaporated. Resulting alcohol was dissolved in 150 ml benzene. To this solution 0.1 g p-toluenesulphonic acid. The resulting mixture was refluxed in 10 min, then was cooled to r.t., washed with saturated aq. NaHCO$_3$ and water. The solution so-obtained was dried over MgSO$_4$ and evaporated to give 1.4 g (67% from ketone) of the solid product.

$^1$H NMR (CD$_2$Cl$_2$): 7.37 (AA'BB' component, 2H); 7.32 (AA'BB' component, 2H); 6.38 (quintet, 1H); 3.06 (br.s., 2H); 2.43 (s, 3H); 2.10 (br.s, 3H).

Example 4

One Pot Synthesis of 2,5-dimethyl-3-(4-chlorophenyl)-6H-cyclopenta[b]thiophene lithium salt

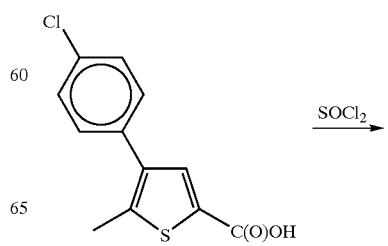

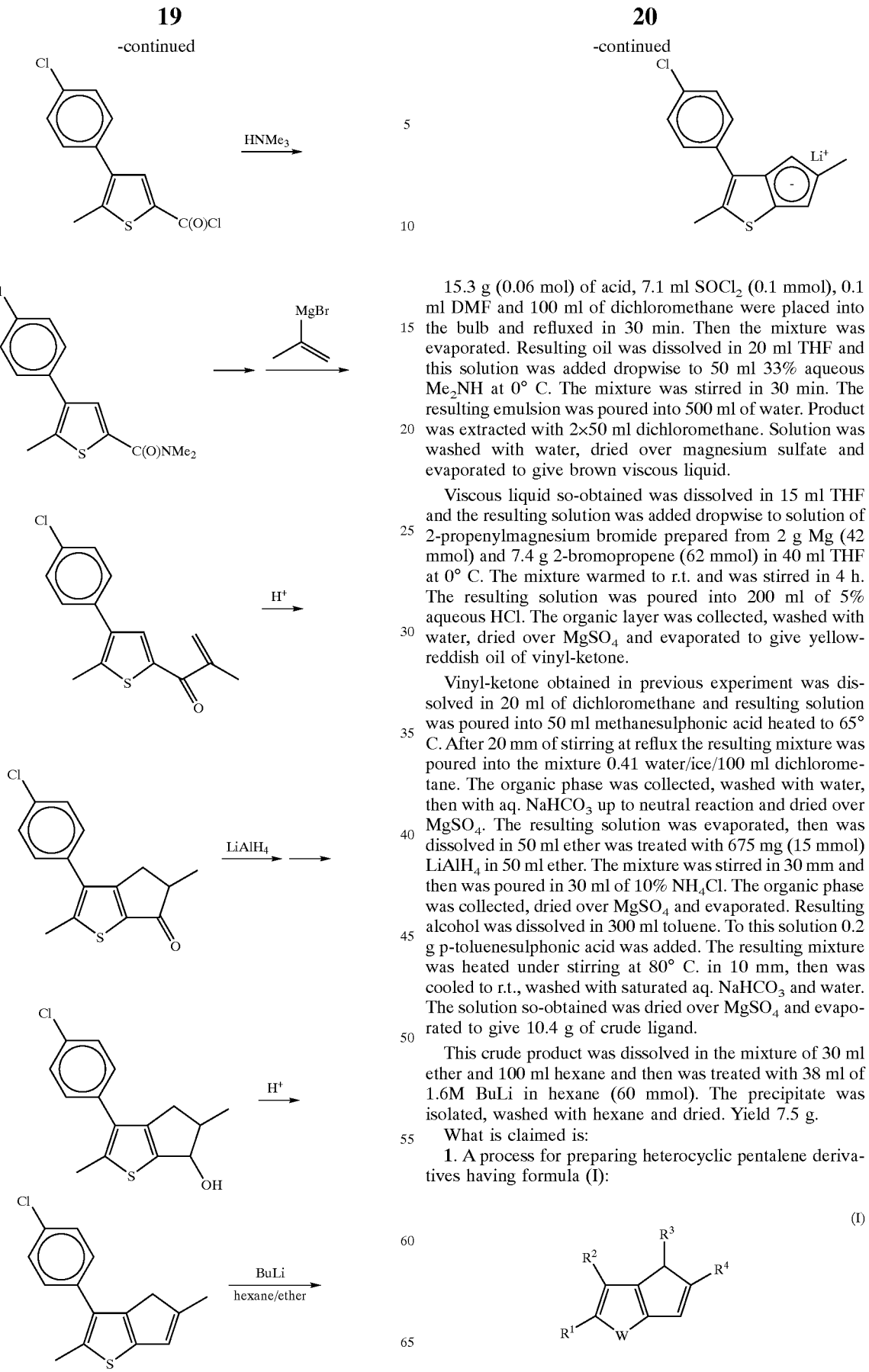

15.3 g (0.06 mol) of acid, 7.1 ml SOCl$_2$ (0.1 mmol), 0.1 ml DMF and 100 ml of dichloromethane were placed into the bulb and refluxed in 30 min. Then the mixture was evaporated. Resulting oil was dissolved in 20 ml THF and this solution was added dropwise to 50 ml 33% aqueous Me$_2$NH at 0° C. The mixture was stirred in 30 min. The resulting emulsion was poured into 500 ml of water. Product was extracted with 2×50 ml dichloromethane. Solution was washed with water, dried over magnesium sulfate and evaporated to give brown viscous liquid.

Viscous liquid so-obtained was dissolved in 15 ml THF and the resulting solution was added dropwise to solution of 2-propenylmagnesium bromide prepared from 2 g Mg (42 mmol) and 7.4 g 2-bromopropene (62 mmol) in 40 ml THF at 0° C. The mixture warmed to r.t. and was stirred in 4 h. The resulting solution was poured into 200 ml of 5% aqueous HCl. The organic layer was collected, washed with water, dried over MgSO$_4$ and evaporated to give yellow-reddish oil of vinyl-ketone.

Vinyl-ketone obtained in previous experiment was dissolved in 20 ml of dichloromethane and resulting solution was poured into 50 ml methanesulphonic acid heated to 65° C. After 20 mm of stirring at reflux the resulting mixture was poured into the mixture 0.41 water/ice/100 ml dichloromethane. The organic phase was collected, washed with water, then with aq. NaHCO$_3$ up to neutral reaction and dried over MgSO$_4$. The resulting solution was evaporated, then was dissolved in 50 ml ether was treated with 675 mg (15 mmol) LiAlH$_4$ in 50 ml ether. The mixture was stirred in 30 mm and then was poured in 30 ml of 10% NH$_4$Cl. The organic phase was collected, dried over MgSO$_4$ and evaporated. Resulting alcohol was dissolved in 300 ml toluene. To this solution 0.2 g p-toluenesulphonic acid was added. The resulting mixture was heated under stirring at 80° C. in 10 mm, then was cooled to r.t., washed with saturated aq. NaHCO$_3$ and water. The solution so-obtained was dried over MgSO$_4$ and evaporated to give 10.4 g of crude ligand.

This crude product was dissolved in the mixture of 30 ml ether and 100 ml hexane and then was treated with 38 ml of 1.6M BuLi in hexane (60 mmol). The precipitate was isolated, washed with hexane and dried. Yield 7.5 g.

What is claimed is:

1. A process for preparing heterocyclic pentalene derivatives having formula (I):

wherein

W is a sulfur atom, an oxygen atom or a NR or PR group wherein R is selected from the group consisting of a linear or branched saturated or unsaturated $C_1$–$C_{20}$-alkyl, $C_3$–$C_{20}$-cycloalkyl, $C_6$–$C_{20}$-aryl, $C_7$–$C_{20}$-alkylaryl and $C_7$–$C_{20}$-arylalkyl radical, optionally containing heteroatoms belonging to groups 13–17 of the Periodic Table of the Elements;

$R^1$, $R^2$, $R^3$ and $R^4$, equal to or different from each other, are hydrogen atoms or a linear or branched saturated or unsaturated $C_1$–$C_{20}$-alkyl, $C_3$–$C_{20}$-cycloalkyl, $C_6$–$C_{20}$-aryl, $C_7$–$C_{20}$-alkylaryl or $C_7$–$C_{20}$-arylalkyl radical, optionally containing heteroatoms belonging to groups 13–17 of the Periodic Table of the Elements; or $R^1$ and $R^2$ and/or $R^3$ and $R^4$ can form a $C_4$–$C_7$ ring optionally containing O, S, N, P or Si atoms, said ring optionally bearing $C_1$–$C_{20}$ alkyl substituents or being optionally fused with a $C_4$–$C_7$ ring optionally containing O, S, N, P or Si atoms;

said process comprising the following steps:

a) contacting a compound of formula (II):

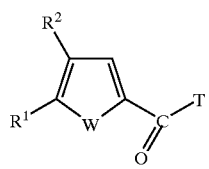

(II)

wherein T is a OR, $NR^2$, OH, $CCl_3$, $CF_3$, Cl, Br, I, imidazolyl or pirazolyl radical, with at least one molar equivalent of a vinyl compound of formula (III):

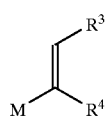

(III)

wherein M is MgHal, Li K or ZnHal, and wherein Hal is chlorine, bromine or iodine, to form a compound of formula (IV):

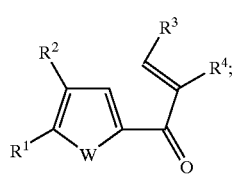

(IV)

b) treating the compound of formula (IV) with a Brønsted acid to form a compound of formula (V):

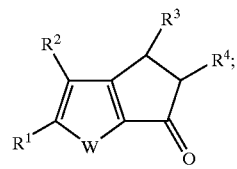

(V)

c) treating the compound of formula (V) with a reducing agent to form the correspondent alcohol of formula (VI):

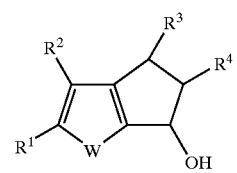

(VI)

and d) dehydrating the alcohol of formula (VI).

2. The process according to claim 1 wherein in the compound of formula (I), the group NR is N-methyl or N-phenyl; the group PR is P-methyl or P-phenyl; $R^1$ is hydrogen, a $C_1$–$C_{20}$-alkyl or $C_7$–$C_{20}$-arylalkyl radical; $R^2$ is hydrogen or a $C_7$–$C_{20}$-arylalkyl radical; $R^3$ is hydrogen or a $C_1$–$C_{20}$-alkyl radical and $R^4$ is hydrogen, a $C_1$–$C_{20}$-alkyl or $C_7$–$C_{20}$-arylalkyl radical.

3. The process according to claim 1 wherein in the compound of formula (I), W is a sulfur atom; $R^1$ is a methyl, a phenyl or a $C_1$–$C_{10}$ alkyl substituted phenyl radical; $R^2$ is a phenyl or a $C_1$–$C_{10}$ alkyl-substituted phenyl radical and $R^4$ is a methyl, or a phenyl radical.

4. The process according to claim 1 wherein in the compound of formula (II), T is a $NR^2$ group and in the compound of formula (III), the group M is MgBr or Li.

5. The process according to claim 1 wherein the Brønsted acid used in step b) are methanesulphonic acid, sulfuric acid, phosphoric acid, polyphosphoric acid or $P_2O_5$/methansulfuric acid.

6. The process according to claim 1 wherein the reducing agent used in step c) is $LiAlH_4$, $AlH_3$, $NaBH_4$ or $LiHAl(OtBu)_3$.

7. The process according to claim 1 wherein the dehydrating agent used in step d) is p-toluenesulfonic acid, sulfuric acid, hydrochloric acid or iodine.

8. The process according to claim 1 wherein the compound obtained in step d) is purified by treating the crude reaction product with at least one equivalent of an organolithium compound and filtering the obtained salt.

9. The process according to claim 1 wherein steps a, b, c and d) are carried out in sequence without purification of the intermediate products.

10. The process according to claim 1 wherein steps c) and d) are carried out without purification of the alcohol of formula (VI).

* * * * *